United States Patent [19]

Brier

[11] Patent Number: 4,552,763
[45] Date of Patent: Nov. 12, 1985

[54] SYNERGISTIC ANTIBACTERIAL COMPOSITIONS AND METHOD OF TREATMENT OF INFECTIONS CAUSED BY MULTIPLE ANTIBIOTIC-RESISTANT ORGANISMS

[75] Inventor: Gordon L. Brier, Indianapolis, Ind.

[73] Assignee: Eli Lilly and Company, Indianapolis, Ind.

[21] Appl. No.: 574,441

[22] Filed: Jan. 27, 1984

Related U.S. Application Data

[60] Division of Ser. No. 332,774, Dec. 21, 1981, Pat. No. 4,452,778, which is a continuation-in-part of Ser. No. 135,390, Mar. 31, 1980, abandoned, which is a continuation-in-part of Ser. No. 36,263, May 4, 1979, abandoned.

[51] Int. Cl.$^4$ ............................................. A61K 35/00
[52] U.S. Cl. ................................................... 424/114
[58] Field of Search ......................................... 424/114

[56] References Cited

U.S. PATENT DOCUMENTS 4,138,486  2/1979  Narisada et al. ............... 424/248.52

OTHER PUBLICATIONS

Modern Drug Encyclopedia, 14 ed., 1977 pp. 53–54.

*Primary Examiner*—Jerome D. Goldberg
*Attorney, Agent, or Firm*—William B. Scanlon; Arthur R. Whale

[57] ABSTRACT

Antibiotic compositions comprising a 1-oxa β-lactam antibiotic compound of the formula

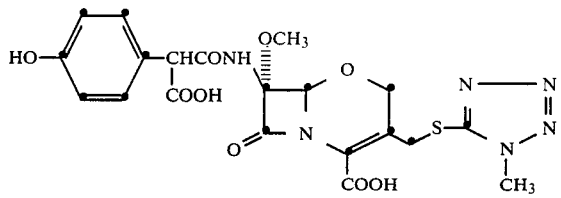

or pharmaceutically acceptable salts thereof and either tobramycin, amikacin or piperacillin exhibit synergistic activity against multiple-antibiotic-resistant organisms. The 1-oxa compound can be used in conjunction with tobramycin, amikacin or piperacillin in a method of treating infections caused by resistant organisms.

8 Claims, No Drawings

SYNERGISTIC ANTIBACTERIAL COMPOSITIONS AND METHOD OF TREATMENT OF INFECTIONS CAUSED BY MULTIPLE ANTIBIOTIC-RESISTANT ORGANISMS

CROSS REFERENCE TO RELATED APPLICATIONS

This application is a division of application Ser. No. 332,774, filed 12-21-81 now U.S. Pat. No. 4,452,778 issued June 5, 1984, which was a continuation-in-part of application Ser. No. 135,390, filed Mar. 31, 1980, now abandoned, which was a continuation-in-part of application Ser. No. 36,263, filed May 4, 1979, now abandoned.

BACKGROUND AND SUMMARY OF THE INVENTION

This invention is directed to antibiotic compositions exhibiting synergistic activity against a number of multiple-antibiotic-resistant organisms, and to a method of treating infections caused by such organisms in man and other warm-blooded animals. More particularly this invention is concerned both with synergistic antibiotic compositions containing moxalactam, the 1-oxa β-lactam antibiotic compound of the formula

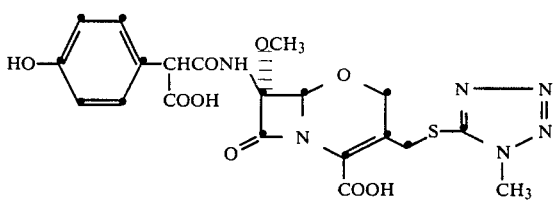

or pharmaceutically acceptable salts thereof and, either tobramycin, amikacin or piperacillin (sodium 6-(D(-)-α-(4-ethyl-2,3-dioxo-1-piperazinylcarbonylamino)-α-phenylacetamido]penicillinate), and with a method of treating infections utilizing the 1-oxa antibiotic compound I in combination with tobramycin, amikacin or piperacillin.

The mutual effect of simultaneously administered antibiotics, exerted on each other and on various pathogenic microorganisms, has been the subject of much research. The literature is replete with reports by investigators whose experiments have shown unambiguously that among previously known antibiotics, either synergism or antagonism may occur. In the case of synergism the antibiotic combination exhibits a marked increase in activity over that which could be predicted as the result of a purely additive effect of the two or more drugs in combination. Both quantitative and qualitative synergistic effects have been observed.

The treatment of infections due to multiple-antibiotic-resistant organisms presents a challenge which a number of clinicians have in the past sought to meet through the utilization of synergistic antibiotic combinations. The lower effective minimum inhibitory concentrations (mics) of synergistic combinations of the present invention as well as others against such organisms allow for the treatment of those more difficult infections at lower dosage levels than otherwise possible, thereby lowering the probability of toxicity complications, the time for treatment, and, potentially, the cost of therapy. The present invention therefore constitutes a significant addition to the physician's medicinal armamentarium.

The antibiotic compounds utilized in the present invention are known compounds. Tobramycin and amikacin or their sulfuric acid addition salts are commercially available broad spectrum aminoglycoside antibiotics. Piperacillin is a relatively new penicillin antibiotic compound. Its preparation is described by I. Saikawa et al. in the *Journal of the Pharmaceutical Society of Japan*, 597, No. 9, p 980–986 (1977). The 1-oxa β-lactam compound designated by formula I above was recently described in U.S. Pat. No. 4,138,486, issued Feb. 6, 1979.

DETAILED DESCRIPTION OF THE INVENTION

The present invention is based on the discovery that the 1-oxa β-lactam antibiotic compound I when combined with either tobramycin, amikacin or piperacillin exhibits synergistic antibiotic activity against a number of strains of multiple-antibiotic-resistant microorganisms. Using the broth dilution technique in a checkerboard distribution it was determined that the 1-oxa compound I when combined with tobramycin exhibited mics of about 0.012 to about 4 mcg/ml against strains of *Pseudomonas aeruginosa, Serratia marcescens, E. coli, E. cloacae, Klebsiella pneumoniae, Proteus rettgeri, Proteus mirabilis, Proteus vulgaris, Pseudomonas maltophilia,* and *Acinetobacter* sp. Similarly it was determined that the 1-oxa compound I when combined with amikacin exhibited mics of about 0.06 to about 8 mcg/ml against strains of *Proteus rettgeri, Klebsiella pneumoniae, Serratia marcescens, E. cloacae, Pseudomonas aeruginosa, Pseudomonas maltophilia, Pseudomonas pseudomallei* and *Acinetobacter* sp. It was also determined that the 1-oxa compound I when combined with piperacillin exhibited mics of about 0.12 to about 16 mcg/ml against strains of *Pseudomonas aeruginosa, Serratia marcescens, E. coli,* and *acinetobacter* sp. Synergistic activity against *Pseudomonas aeruginosa* strains is especially notable in combinations of the 1-oxa compound and tobramycin or piperacillin.

Clinical advantage of the observed synergistic activity can be realized, therefore, by administering the 1-oxa compound I or a pharmaceutically acceptable salt thereof in conjunction with either tobramycin, amikacin or piperacillin at dosages that will provide synergistically therapeutic blood levels of each antibiotic. Generally speaking it can be said that against a given organism the therapeutic level of a compound in the blood is that level equal to or greater than the minimum inhibitory concentration measured for that compound by in vitro studies. To assure the efficiency of the 1-oxa compound when used in combination with tobramycin, amikacin or piperacillin in the method of this invention, minimum blood levels for the 1-oxa compound are preferably at least twice the in vitro-measured combination mic for that compound.

Thus one feature of the present invention is a method of treating infections caused by multiple-antibiotic resistant Gram-negative organisms in a warm-blooded animal which comprises administering to said animal the 1-oxa compound I or a pharmaceutically acceptable salt thereof in an amount sufficient to produce blood levels of said compound in said animal of at least about 0.02 to about 8 mcg/ml; and administering in conjunction therewith a synergistically effective amount of tobramycin.

A further embodiment of the present invention is a method of treating infections caused by multiple-antibiotic resistant Gram-negative organisms in a warm-blooded animal which comprises administering to said animal the 1-oxa compound I or a pharmaceutically acceptable salt thereof in an amount sufficient to produce blood levels of said compound in said animal of at least about 0.12 to about 16 mcg/ml; and administering in conjunction therewith a synergistically effective amount of amikacin.

Another embodiment of the present invention is a method of treating infections caused by multiple-antibiotic-resistant Gram-negative organisms in a warm-blooded animal which comprises administering to said animal the 1-oxa compound I or a pharmaceutically acceptable salt thereof in an amount sufficient to produce blood levels of said compound in said animal of at least about 0.2 to about 32 mcg/ml; and administering in conjunction therewith a synergistically effective amount of piperacillin.

The term "multiple-antibiotic-resistant Gram-negative organisms" as used herein refers to those Gram-negative organisms that have shown resistance to several classes (for example, penicillins, cephalosporins, aminoglycosides, macrolides etc.) of antibiotic compounds.

A "synergistically effective amount" as used in the foregoing description of the method embodiments of the present invention refers to that amount of antibiotic (piperacillin, amikacin or tobramycin) which will on administration provide concentration of that antibiotic in the blood equal to or above the minimum concentration necessary for synergistic co-action of that antibiotic and the 1-oxa compound at the level administered in conjunction therewith. In this regard it should be noted that results of combination synergy studies are reported in terms of minimum inhibitory concentrations of each compound when tested in combination with the others. These values are regarded simply as an indicator of the presence (or absence) of synergistic co-action of the combined antibiotics. If synergy is in fact indicated by the combination mics, the combined antibiotics will usually display synergistic activity over a wide range of concentrations of each antibiotic. Analogously synergistic activity can be exploited in vivo over a wide range of blood serum levels for each antibiotic. Thus, for example, for any given blood level, equal to or above about twice the in vitro 1-oxa compound-tobramycin combination mic of the 1-oxa compound, clinical advantage of the synergistic activity can be had over a range of tobramycin blood levels.

The dosage required of any of the antibiotic compounds utilized in the present method to achieve the desired synergistically therapeutic blood levels depends on a number of factors including animal or patient weight, the nature of the infection, the particular method of administration, and the pharmacokinetics of the particular antibiotics.

The pharmacokinetics or more particularly the blood level-dose response for tobramycin is well documented. [See for example the *Physicians' Desk Reference*, 33rd Edition, published 1979, by Medical Economics, Inc., a division of Litton Industries, Inc., Oradel, N.J., pages 1043–1045]. Following an intramuscular dose of 1 mg/kg of tobramycin sulfate maximum serum concentrations reach about 4 mcg/ml. For example, peak serum concentrations of tobramycin in healthy volunteers receiving a single 1 mg/kg (i.m.) were 4.4 mcg/ml. Single doses of tobramycin (sulfate) for the present method range from about 0.6 to about 2 mg/kg and more preferably from about 0.6 to about 1.5 mg/kg. Such dosages provide blood levels of tobramycin at synergistically effective concentrations of between at least about 0.5 mcg/ml to about 8 mcg/ml.

The blood level-dose response for amikacin is likewise well-documented. See the *Physicians' Desk Reference*, 34th Edition, published 1980, by Medical Economics, Inc., a division of Litton Industries, Inc., Oradel, N.J., pages 701–703. Average peak serum concentrations of about 12, 16 and 21 mcg/ml are obtained 1 hour after intramuscular administration of 250 mg (3.7 mg/kg), 375 mg (5 mg/kg), 500 mg (7.5 mg/kg) single doses respectively. At 10 hours serum levels are about 0.3, 1.2 and 2.1 mcg/ml respectively. Single doses of 500 mg (7.5 mg/kg) administered to normal adults as an infusion over a period of 30 minutes produced a mea peak serum concentration of amikacin of 38 mcg/ml at the end of the infusion and levels of 24 mcg/ml, 18 mcg/ml and 0.75 mcg/ml after 30 minutes, 1 hour and 10 hours post-infusion respectively. Single doses of amikacin (sulfate) for the present method range from about 1 mg/kg to about 6 mg/kg and more preferably from about 1 mg/kg to about 3 mg/kg with the particular dose being dependent on patient weight, the infecting organism and the method of administration. According to this embodiment, synergistically effective blood levels of amikacin of about 0.5 mcg/ml to about 8 mcg/ml are provided by the above dosages.

Several investigators have studied extensively the pharmacokinetics of piperacillin [M. A. Evans et al., *Journal of Antimicrobial Chemotherapy*, 4, 255–261 (1978) and T. B. Tjandramaga et al., *Antimicrobial Agents and Chemotherapy*, Vol. 14, No. 8, 829–837 (1978)]. Single intramuscular doses of 0.5, 1.0, and 2.0 g of piperacillin resulted in mean peak serum concentrations of 4.9, 13.3 and 30.2 mcg/ml respectively. Single intravenous bolus doses of 1.0, 2.0, 4.0 and 6.0 g of piperacillin provided mean serum concentrations of 70.7, 199.5, 330.7 and 451.8 mcg/ml respectively at the end of the injections. The antibiotic has a mean terminal serum half-life of 60 to 80 minutes after the intramuscular doses and 36 to 63 minutes after the intravenous administration depending on the dose. Single doses of piperacillin for the present method range from about 250 mg to about 4 g and more preferably from about 250 mg to about 2 g.

Serum level response to various intravenous doses of the 1-oxa compound I is summarized in Table I.

TABLE I

| MEAN SERUM CONCENTRATIONS* OF 1-OXA COMPOUND I | | | | | | | | | | | |
|---|---|---|---|---|---|---|---|---|---|---|---|
| | Time in hours | | | | | | | | | | |
| Dose** | 1/6 | ⅓ | ½ | 1 | 2 | 3 | 5 | 7 | 9 | 11 | 12 |
| 250 mg IV | 10.9 | 19.8 | 17.7 | 16.4 | 12.4 | 6.3 | 3.2 | 1.5 | 1.4 | | |
| 500 mg IV | 17.1 | 28.4 | 27.2 | 22.9 | 16.9 | 7.5 | 4.6 | 2.6 | | | |
| 1 gm IV | 34.9 | 68.2 | 46.6 | 24.7 | 20.5 | 15.6 | 8.9 | 6.1 | 1.5 | 1.2 | |

TABLE I-continued
MEAN SERUM CONCENTRATIONS* OF 1-OXA COMPOUND I

| Dose** | Time in hours | | | | | | | | | | |
|---|---|---|---|---|---|---|---|---|---|---|---|
| | 1/6 | ⅓ | ½ | 1 | 2 | 3 | 5 | 7 | 9 | 11 | 12 |
| 2 gm IV | 101.8 | 152.2 | 135.8 | 89.2 | 48.7 | 31.2 | 26.1 | 8.7 | 4.0 | | |

*mcg/ml
**Infused over 20 minute period

Thus a 250 mg intravenous dose of the 1-oxa compound will provide serum levels of from about 10 to about 20 mcg/ml for a 2 hour period. The *minimum* serum levels of the 1-oxa compound I necessary for synergistic activity according to the present method range from about 0.02 mcg/ml to about 32 mcg/ml. These minimum serum levels can be easily achieved and even exceeded by the administration of single doses of about 250 mg to about 2 g and more preferably about 250 mg to about 1 g of the 1-oxa compound I. Those skilled in the art can optionally adjust the dose of the 1-oxa compound below or above these levels in accordance with their evaluation of each clinical case. According to this embodiment, synergistically effective blood levels of piperacillin are between about 0.5 mcg/ml to about 32 mcg/ml.

In carrying out the present method two antibiotics are administered to a warm-blooded animal in conjunction with one another to achieve a potentiated antibiotic effect. The antibiotic compounds can be administered intramuscularly or by intravenous infusion of bolus injection, either sequentially or simultaneously through the same or different routes of administration.

The present method can alternatively be carried out by the parenteral administration, in doses of about 250 mg to about 2 g, of a synergistic antibacterial composition comprising 1 part by weight, as the diacid, of the 1-oxa compound I or a pharmaceutically acceptable salt thereof; and from about 0.02 to about 0.6 parts by weight of tobramycin, from about 0.04 to about 2 parts by weight of amikacin, or from about 0.1 to about 16 parts by weight of piperacillin. Such synergist antibacterial compositions constitute additional embodiments of the present invention. The preparation of the compositions according to the present invention may be carried out by methods known in the pharmaceutical arts.

Dosages of the 1-oxa compound I in conjunction with tobramycin, amikacin or pipercillin, administered as synergistic antibacterial compositions or as discrete quantities of the separate compounds can be repeated once every 4–12 hours until the infection is eliminated.

The biological activity (in vitro) of the antibiotic combinations according to the present invention is demonstrated by the following described procedure.

EXPERIMENTAL METHOD FOR DETERMINING SYNERGY

Media used was Mueller-Hinton Broth (BBL) supplemented 20 mg Mg++/L and 80 mg Ca++/L. Antibiotics used for this test were the 1-oxa compound I, tobramycin and pipercillin. A stock solution of pipercillin was prepared by dissolving a weighed amount of laboratory standard in pH 7 phosphate buffer to give a concentration of 1000 ug/ml. Stock solution of compound I was prepared by dissolving the contents of one vial of pre-weighed (10 mg) laboratory standard in 10 ml of pH 7 phosphate buffer. Tobramycin is supplied as a solution containing 1 mg/ml. Working solution of the antibiotics was made by diluting the stock solutions with supplemented Mueller-Hinton broth.

The checkerboard tube dilution technique was adapted to the microtiter system using Autotiter plates containing 120 wells per plate. The plate has eight columns of 15 wells. The columns of the plates are designated A through H and the rows of wells are numbered 1 through 15. The addition of the diluent (supplemented Mueller-Hinton broth containing antibiotic) and the two-fold serial dilution of antibiotics were done using an Autotiter V (Ames). With Autotiter system, it is possible to dispense into the wells in each of the eight columns of the plate media containing different concentrations of antibiotic (Antibiotic A). Eight tubes of media containing two-fold serial dilutions of antibiotic A were prepared and placed in the dispensing jar of the multiple reagent dispenser. The antibiotic B to be tested in combination with the antibiotic A was placed in the antibiotic pickup tray in the Autotiter. All eight wells in the antibiotic pickup tray contain the same concentration of antibiotic B. Two-fold serial dilution of antibiotic B were made in the media containing antibiotic A. Two-fold dilutions of antibiotic A were made in rows 1 through 13; row 14 contains media without antibiotic and row 15 contains media plus antibiotic. The diluted plate contains a two-fold serial dilution of antibiotic B in constant concentration of antibiotic A (each column) in rows 1 through 13 with the columns A through H containing a serial two-fold dilution of antibiotic A in a decreasing concentration. The antibiotic concentrations made were chosen so that the range of concentration in the diluted plate spanned the range of the minimum inhibitory concentrations (mic) of each individual antibiotic for each of the isolates tested. Fifty ul of diluent was dispensed into each well.

The inoculum was prepared from an overnight broth. The overnight cultures turbidity was adjusted to a MacFarland 0.5 turbidity standard ($10^8$ cfu). The standard is prepared by adding 0.5 ml of 0.048M $BaCl_2$ to 99.5 ml of 0.35N $H_2SO_4$. Further dilution of the standardized overnight broth culture is made to give a final concentration of $10^5$ colony forming units. Fifty ul of this inoculum was added using 50 ul dropping pipettes to each of wells in columns A through H and rows 1 through 14. Row 14 contains no antibiotic and is used as a growth control; row 15 is not inoculated and is used as a sterility control. The final volume in each well in rows 1 through 14 is 100 ul. After inoculation, the plates are sealed with plastic tape and incubated at 35° C. for 18 to 24 hours. After incubation, the plates are read using an Autotiter viewer. The turbid well containing only organism and media (row 14) is used for comparison in determining growth end points.

The lowest concentration of antibiotic showing complete inhibition of growth is the mic. The mic for the individual antibiotics for each isolate being tested was confirmed at the time of testing for synergistic combinations using a microdilution technique. The results of the synergy studies of combinations of the 1-oxa compound I and tobramycin or pipercillin against a number of strains of multiple-antibiotic-resistant Gram-negative organisms are summarized in Table II, while the results of synergy studies of 1-oxa compound I-amikacin combinations are provided in Table III.

TABLE II

Results of Synergy Studies of Combinations of the 1-Oxa Compound I and Tobramycin or Pipericillin

| Organism | I Alone (mcg/ml) | T* Alone (mcg/ml) | P* Alone (mcg/ml) | Combined I (mcg/ml) | T | Combined I (mcg/ml) | P |
|---|---|---|---|---|---|---|---|
| *Ps. aeruginosa* | | | | | | | |
| 1484 | 64 | 64 | 64 | 4 | 2 | 16 | 8 |
| 447 | 32 | 64 | >128 | <0.5 | <0.5 | 4 | 0.5 |
| 424 | 8 | 64 | >128 | 2 | 0.5 | 2 | 0.5 |
| 366 | 16 | 4 | >128 | 0.5 | 2 | 8 | 16 |
| 84 | 16 | 8 | 64 | 2 | 1 | 4 | 4 |
| Davis | >64 | >64 | >64 | 2 | 1 | 8 | 16 |
| *S. marcescens* | | | | | | | |
| 100 | 0.25 | 16 | >64 | 0.12 | 8 | 0.12 | 32 |
| 14142 | 1 | >64 | >64 | 0.25 | 4 | 0.12 | 8 |
| 302-2 | 1 | 16 | >64 | 0.12 | 1 | 0.12 | 8 |
| Townsend | 4 | 32 | >64 | 1 | 0.5 | 2 | 64 |
| 796 | 8 | 64 | >64 | 2 | 16 | 2 | 4 |
| *E. cloacae* | | | | | | | |
| 1253 | 4 | 32 | >64 | 0.25 | 2 | 2 | 32 |
| 1415 | 0.12 | 32 | >64 | 0.12 | <0.015 | ** | |
| B293 | 0.5 | >64 | >64 | 0.12 | 8 | 0.25 | 16 |
| 1246 | 0.25 | 16 | >64 | <0.12 | 0.5 | ** | |
| *K. pneumoniae* | | | | | | | |
| 214-1 | 2 | 32 | >64 | 0.012 | 0.03 | 0.5 | 8 |
| 463 | 2 | 16 | >64 | 0.012 | <0.015 | 2 | 16 |
| 1204-2 | 2 | >64 | >64 | 0.012 | 0.03 | 0.5 | 2 |
| 512 | 0.5 | >64 | >64 | 0.012 | 0.06 | 0.5 | 32 |
| 933 | 0.25 | 32 | >64 | <0.012 | 0.5 | ** | |
| 130 | 0.5 | 16 | >64 | <0.012 | 0.5 | ** | |
| *P. rettgeri* | | | | | | | |
| 65 | 0.25 | 64 | 64 | 0.12 | 1 | ** | |
| *P. mirabilis* | | | | | | | |
| Allen | 0.06 | 32 | >64 | <0.12 | 1 | ** | |
| *P. Vulgaris* | | | | | | | |
| Shide | 0.06 | 32 | >64 | <0.12 | 1 | ** | |
| 363 | 0.12 | 64 | >64 | <0.12 | 1 | ** | |
| *E. coli* | | | | | | | |
| Dill | 0.25 | >64 | 32 | <0.12 | 4 | ** | |
| 1262 | 0.03 | 16 | >64 | <0.12 | 8 | <0.12 | 64 |
| 136-3 | 0.06 | 64 | >64 | <0.12 | 4 | ** | |
| Briley | 0.12 | 4 | >64 | <0.12 | 8 | <0.12 | 32 |
| 1415 | ** | ** | ** | <0.12 | 8 | <0.12 | 2 |
| 46-2 | 0.03 | >64 | >64 | <0.12 | 4 | <0.12 | 2 |
| 1253 | ** | ** | ** | <0.12 | 4 | 0.5 | 4 |
| 1260 | 0.03 | >64 | >64 | <0.12 | 0.5 | ** | |
| 77-3 | 0.03 | 64 | >64 | <0.12 | 0.25 | ** | |
| *Ps. maltophilia* | | | | | | | |
| 10 | 32 | 64 | ** | 4 | 8 | | |
| 505 | 8 | 32 | | 0.6 | 0.5 | | |
| 11 | 4 | 4 | | 0.5 | 2 | | |
| *Acinetobacter sp.* | | | | | | | |
| 28-1 | 16 | 0.5 | ** | 0.6 | 0.5 | | |
| 106 | 8 | 1 | | 0.6 | 0.5 | | |
| 28-2 | 16 | 4 | | 2 | 0.5 | | |
| 107 | 32 | 4 | | 2 | 0.5 | | |
| 109 | 16 | 1 | | 2 | 0.5 | | |

*T = tobramycin
P = pipericillin
**Not tested

TABLE III

Results of Synergy Studies of Combinations of the 1-Oxa Compound I and Amikacin

| Organism Isolate | I* Alone (mcg/ml) | A* Alone (mcg/ml) | Combined I (mcg/ml) | A |
|---|---|---|---|---|
| *P. rettgeri* | | | | |
| 768 | 0.5 | 16 | <0.06 | <0.5 |
| 53 | 0.25 | 8 | <0.06 | <0.5 |
| 997 | 0.4 | 8 | <0.06 | <0.5 |
| 1422 | 2 | 4 | 2 | 8 |
| 136-1 | 0.25 | 4 | 0.12 | 1 |
| *K. pneumoniae* | | | | |
| 938 | 0.25 | 4 | <0.06 | <0.5 |
| 130 | 0.5 | 4 | 0.5 | <0.5 |
| 214-1 | 2 | 8 | <0.06 | <0.5 |
| 463 | 2 | 2 | 2 | <0.5 |
| 1231 | 0.5 | 4 | 0.06 | 2 |
| *S. marcescens* | | | | |
| ziegler | 4 | 4 | 0.06 | 2 |

TABLE III-continued
Results of Synergy Studies of Combinations of the 1-Oxa Compound I and Amikacin

| Organism Isolate | I* Alone (mcg/ml) | A* Alone (mcg/ml) | Combined I (mcg/ml) | Combined A (mcg/ml) |
|---|---|---|---|---|
| 463-2 | 8 | 1 | <0.06 | <0.5 |
| 606 | 4 | 1 | 0.5 | <0.5 |
| B377 | 8 | 2 | 0.12 | <0.5 |
| 1414 | 1 | 8 | 0.06 | <0.5 |
| E. cloacae | | | | |
| 1253 | 4 | 1 | <0.06 | <0.5 |
| 1415 | 0.12 | 8 | 0.12 | <0.5 |
| 228 | 0.12 | 2 | <0.06 | <0.5 |
| 1296 | 0.25 | 4 | 0.06 | 0.5 |
| McQuinn | 0.25 | 32 | 0.12 | 2 |
| Ps. aeruginosa | | | | |
| 362 | 32 | 16 | 4 | 2 |
| 316-2 | 8 | 16 | 4 | 2 |
| 610 | >64 | 1 | 0.6 | 1 |
| 363 | 32 | 32 | 1 | 2 |
| Brownlee | 32 | 16 | 1 | 4 |
| Ps. maltophilia | | | | |
| 10 | 32 | >64 | 8 | <0.5 |
| 505 | 8 | >64 | 2 | 1 |
| Ps. pseudomallei | 32 | 32 | 4 | 8 |
| Acinetobacter sp. | | | | |
| 28-1 | 16 | 8 | 2 | 8 |
| 106 | 8 | 2 | <0.06 | <0.5 |
| 28-2 | 16 | 4 | <0.06 | <0.5 |
| 107 | 32 | 8 | 8 | 8 |
| 109 | 16 | 4 | 8 | <0.5 |

*A = amikacin

The results are expressed in terms of mic for each drug in the combination. A four-fold decrease in concentration of each of the two combined drugs from the concentration of the individual drugs required to obtain the specified effect is generally considered as acceptable evidence of synergism. However varying degrees of synergism can be detected and expressed in terms of the Fractional Inhibitory Concentration (FIC) or the Fractional Bactericidal Concentration (FBC). The FIC, or the FBC, for each drug can be calculated by dividing the concentration of each antibiotic present in the combination by the amount of each drug alone required for the same effect. Thus if $A_m$ and $B_m$ are the mics of drugs A and B alone against a given organism, and $A_c$ and $B_c$ are the mic's against that same organism of the respective drugs in the combination at the point of maximum effectiveness, then $$FIC = FBC = FIC_a + FIC_b = \frac{A_c}{A_m} + \frac{B_c}{B_m}$$

The degree of synergism exhibited is inversely proportional to the combination FIC (the sum of $FIC_a$ and $FIC_b$). Where the FIC is less than 1 some synergy is indicated. Of course, the smaller the combination FIC value the greater the degree of synergism indicated. As the FIC value approaches 1, a purely additive effect is indicated. An FIC of greater than 1 is indicative of antagonism. A four-fold decrease in the mic of each drug in the combination results in an FIC of 0.5.

The present invention is further illustrated by the following examples.

EXAMPLE 1

A patient suffering from a resistant Pseudomonas aeruginosa infection is treated by the sequential intravenous administration of 500 mg of the 1-oxa compound I and 60 mg of tobramycin. Treatment is repeated every 8 hours.

EXAMPLE 2

A patient suffering from an infection caused by Klebsiella pneumoniae is treated by administering intramuscularly 750 mg of the 1-oxa compound and by intravenous infusion 1 g of piperacillin.

EXAMPLE 3

A patient suffering from a Pseudomonas aeruginosa infection is treated by administering sequential intramuscular injections of sterile solutions of 1 g of the 1-oxa compound and 1 g of piperacillin. Treatment is repeated about every 12 hours.

EXAMPLE 4

A patient suffering from an infection caused by Serratia marcescens is treated by the intravenous infusion of 250 mg of the 1-oxa compound I as a sterile solution of its disodium salt and concommitant intramuscular administration of 90 mg of tobramycin sulfate.

EXAMPLE 5

100 Grams of the 1-oxa compound as its disodium salt and 200 grams of piperacillin are combined and blended. 1 Gram portions of the resulting composition are sealed in ampules.

EXAMPLE 6

A patient suffering from an infection caused by Pseudomonas aeruginosa is treated by intramuscular administration of 1 g of the composition of Example 5 in a suitable sterile diluent.

EXAMPLE 7

50 Grams of the 1-oxa compound as its disodium salt and 10 grams of tobramycin sulfate are combined and blended. 1 Gram portions of the resulting composition are sealed in ampules.

EXAMPLE 8

A patient suffering from an infection caused by Pseudomonas aeruginosa is treated by intramuscular administration of 1 g of the composition of Example 7 in a suitable sterile diluent.

EXAMPLE 9

A patient suffering from an infection caused by Serratia marcescens is treated by the sequential intramuscular administration of 250 mg. of the 1-oxa compound I as its disodium salt in a sterile solution and 150 mg. of amikacin sulfate in a sterile solution. Treatment is repeated every 6 hours.

EXAMPLE 10

A patient suffering from an infection caused by Klebsiella pneumoniae is treated by concommitant intravenous infusion of separate sterile solutions of 350 mg. of the disodium salt of the 1-oxa compound I and 100 mg. of amikacin sulfate. Treatment is repeated every 8 hours.

EXAMPLE 11

500 Grams of the 1-oxa compound I as its disodium salt and 100 grams of amikacin sulfate are combined and blended. 1-Gram portions of the resulting composition are sealed in sterile ampules.

EXAMPLE 12

A patient suffering from an infection caused by *Pseudomonas aeruginosa* is treated by intramuscular administration of 1 gram of the composition of Example 11 in a suitable sterile diluent. Treatment is repeated every 8 hours.

I claim:

1. A method of treating infections caused by multiple-antibiotic-resistant gram-negative organisms in a warm-blooded animal which comprises administering to said animal a 1-oxa antibiotic compound of the formula

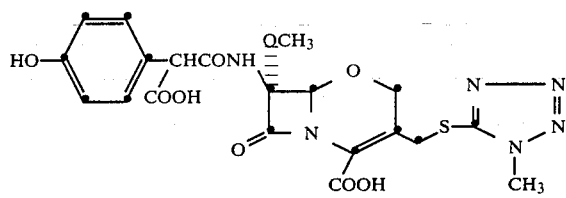

or a pharmaceutically acceptable salt thereof in an amount sufficient to produce blood levels of said compound in said animal of at least about 0.12 to about 16 mcg/ml; and administering in conjunction with said 1-oxa antibiotic amikacin in an amount sufficient to produce blood levels of amikacin in said animal of between about 0.5 mcg/ml and about 8 mcg/ml.

2. The method of claim 1 wherein the multiple-antibiotic-resistant gram-negative organism is selected from the group consisting of *Proteus rettgeri, Klebsiella pnemmoniae, Serratia marcescens, E. cloacae, Pseudomonas aeruginosa, Pseudomonas maltophilia, Pseudomonas pseudomallei* and *Acinetobacter*.

3. A method according to claim 2 for the treatment of infections of *Serratia marcescens*.

4. The method of claim 1 wherein said 1-oxa antibiotic blood levels are produced by administering between about 250 mg to about 2 g of the 1-oxa compound.

5. The method of claim 4 wherein said amikacin blood levels are produced by administering between about 1 mg/kg to about 6 mg/kg of amikacin.

6. The method of claim 4 wherein the dosage of amikacin is about 1 mg/kg to about 3 mg/kg.

7. A synergistic antibacterial composition comprising 1 part by weight, as the diacid, of a 1-oxa compound of the formula

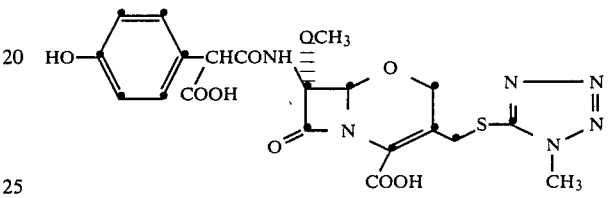

or a pharmaceutically acceptable salt thereof and from about 0.04 to about 2 parts by weight of amikacin.

8. A method of treating infections caused by multiple-antibiotic-resistant gram-negative organisms in a warm-blooded animal which comprises administering to said animal an antibiotically effective amount of a composition of claim 7.

* * * * *